United States Patent [19]

Klein

[11] Patent Number: 5,016,766

[45] Date of Patent: May 21, 1991

[54] ANTI-CONTAMINATION ORTHODONTIC DEVICE DISPENSER

[76] Inventor: Paul E. Klein, 928 Lake Shore Rd., Lak Oswego, Oreg. 97034

[21] Appl. No.: 359,988

[22] Filed: May 31, 1989

[51] Int. Cl.⁵ .......................... A61C 7/00; B65G 59/06
[52] U.S. Cl. ..................................... 221/22; 221/283; 221/312 A
[58] Field of Search ................... 221/22, 92, 240, 283, 221/303, 305, 312 A; 433/3, 8, 11, 18

[56] References Cited

U.S. PATENT DOCUMENTS

| | | | |
|---|---|---|---|
| 755,001 | 3/1904 | Henderson | 221/240 X |
| 1,018,845 | 2/1912 | Miller | 221/312 A X |
| 2,851,192 | 9/1958 | Mayo et al. | 221/283 X |
| 4,038,753 | 8/1977 | Klein | 433/11 |
| 4,530,445 | 7/1985 | Decker | 221/312 A X |
| 4,946,482 | 7/1990 | Johnson | 221/240 |

FOREIGN PATENT DOCUMENTS 1365369   3/1965   France ............................ 221/303

Primary Examiner—F. J. Bartuska
Attorney, Agent, or Firm—Kolisch, Hartwell, Dickinson, McCormack & Heuser

[57] ABSTRACT

The invented anti-contamination orthodontic device dispenser includes a container for housing orthodontic devices, an aperture in the container through with the devices are dispensed, and a guide structure which directs the devices to the aperture for dispensing. The dispenser is gravity and friction controlled so that when one device is dispensed, the next device is presented and ready for dispensing. The container and guide structure are constructed so that the devices are stacked on top of each other and touching because of gravity. Each device has a tooth on its upper surface and ridges on its lower surface. When a device is dispensed, its tooth contacts the ridges on the device immediately above it creating friction which positions the next device for dispensing. The invented dispenser is particularly effective for dispensing orthodontic O-rings mounted on a carrier or stick.

10 Claims, 2 Drawing Sheets

ANTI-CONTAMINATION ORTHODONTIC DEVICE DISPENSER

TECHNICAL FIELD

This invention relates to an orthodontic device dispenser and, more particularly, to a dispenser that protects orthodontic devices from contamination.

BACKGROUND ART

There has recently been a concern in the medical fields about cross-contamination between patients. Particularly, persons who work with patients suffering from an affliction have tried to protect other patients and themselves from being exposed to the affliction. One specific area with a high potential for cross-contamination is orthodontics.

While working on a patient, an orthodontist might employ several devices. Accordingly, the orthodontist may reach from a patient's mouth, select a device and then continue working on the patient. If, while selecting the device, the orthodonist touches other devices or the packaging of the devices, they may be contaminated. Subsequently, when the orthodonist works on another patient, reaches for the same device or an adjacent device and then returns to work, the new patient may be exposed to the contamination.

For example, orthodontic O-rings are often packaged together in selected quantities to minimize the packaging costs. When an orthodontist reaches into a package of O-rings to select some for use, he risks touching and contaminating the remaining stock. Thereafter, any use of the remaining stock may result in cross-contamination between patients.

To prevent contamination, orthodontic devices may be individually packaged. Nevertheless, the orthodontist must still touch each individual package to expose the device. Additionally, it is more expensive for manufactures to individually package orthodontic devices. Alternatively, each device can be sterilized, but sterilization is time consuming and expensive.

The invented anti-contamination orthodontic device dispenser allows manufacturers to package "patient-specific" selected quantities of devices, organized into cohesive dispense-groups each containing a predetermined quantity of devices—such quantity being that typically expected to be, at the most, required for a single treatment session for each individual patient. The dispenser also allows an orthodontist to select such a dispense-group of devices without touching either the dispenser or the remaining clean stock of devices. Accordingly, the invention protects devices from contamination without requiring individual packaging or sterilization.

DISCLOSURE OF THE INVENTION

The invented anti-contamination orthodontic device dispenser includes a container for housing orthodontic devices, an aperture in the container through with the devices are dispensed, and a guide structure which directs the devices to the aperture for dispensing. The dispenser is gravity and friction controlled so that when one device is dispensed, the next device is presented and ready for dispensing.

The container and guide structure are constructed so that the devices are stacked on top of each other and touching because of gravity. Each device has a tooth on its upper surface ridges on its lower surface. When a device is dispensed, its tooth contacts the ridges on the device immediately above it creating friction which positions the next device for dispensing.

The invented dispenser is particularly effective for dispensing orthodontic O-rings mounted on a carrier or stick to form what was referred to above as a patient-specific dispense-group.

DETAILED DESCRIPTION AND BEST MODE FOR CARRYING OUT THE INVENTION

Figure 1:
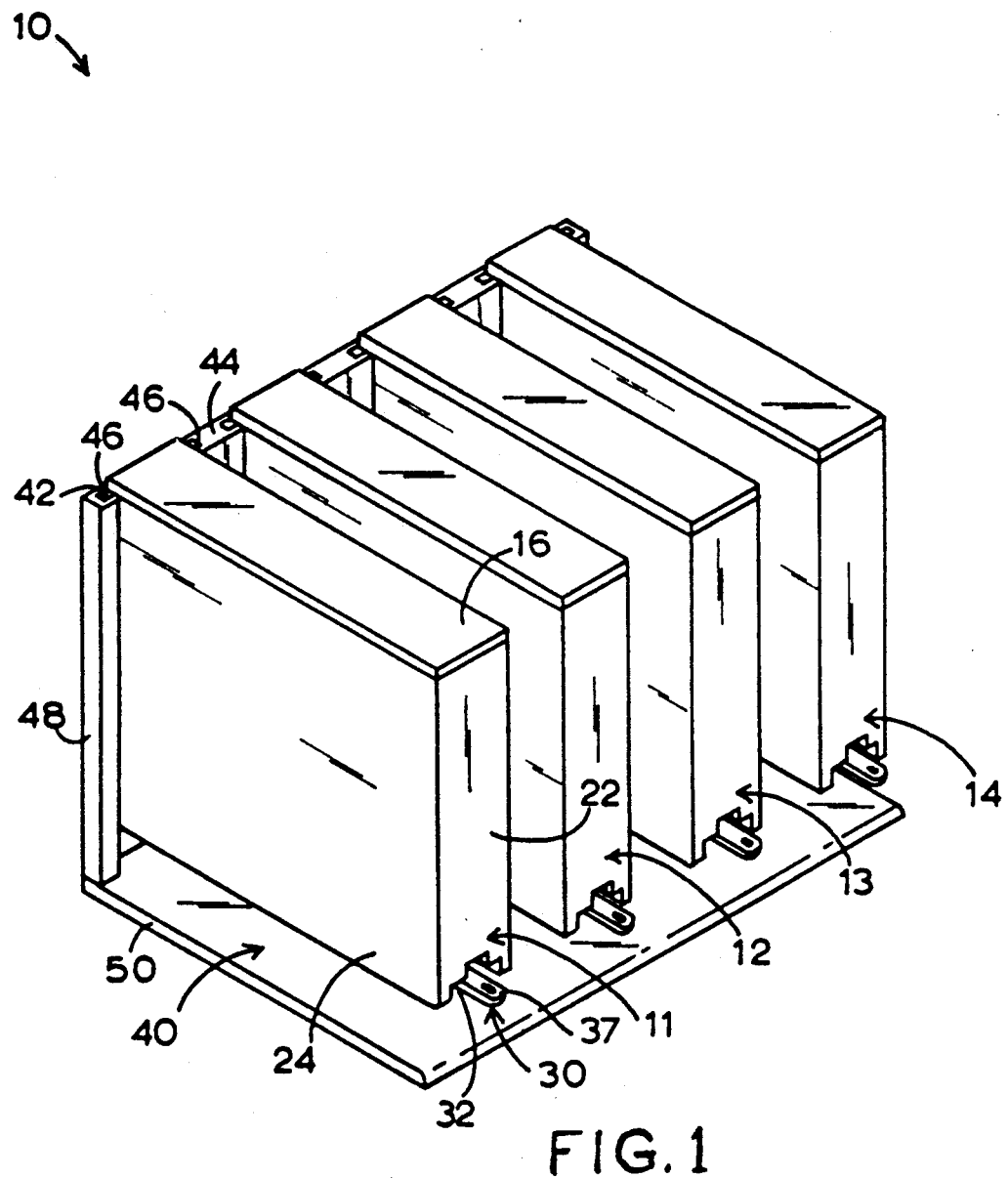
FIG. 1 is a perspective view of one embodiment of the invented dispenser.

One embodiment of the invented anti-contamination orthodontic device dispenser is shown generally at 10 in FIG. 1. Dispenser 10 includes four anti-contamination containers or modules 11, 12, 13, 14 (also referred to an a magazine housing). Other embodiments of dispenser 10 may include only one or many different modules. Modules 11–14 are rectangular boxes which may be made of plastic.

Figure 2:
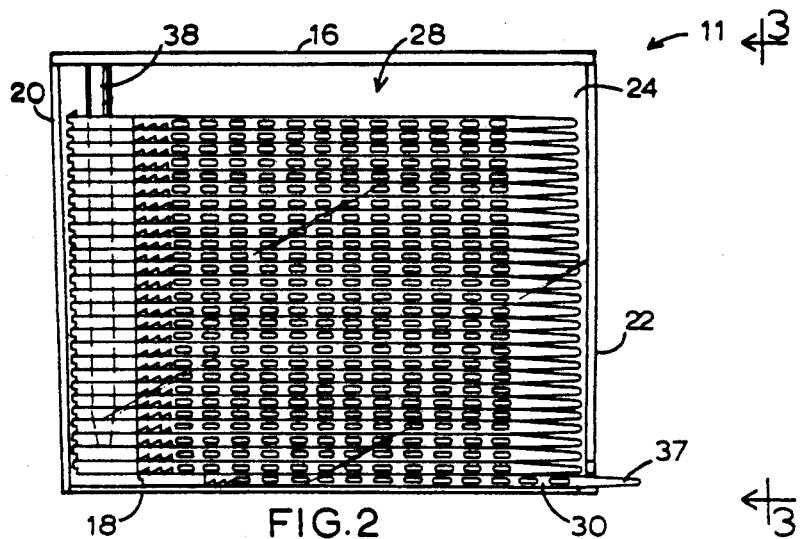
FIG. 2 is a side, plan view of one module or container used in the invented dispenser.
Figure 3:
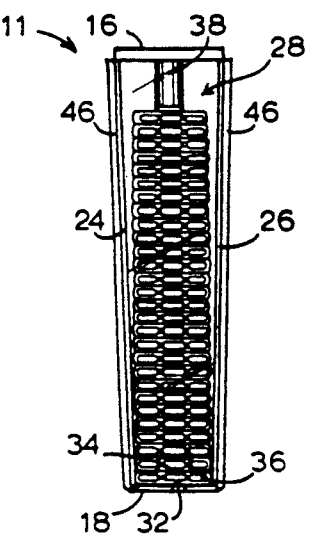
FIG. 3 is an end view of the module shown in FIG. 2, taken along line 3—3.
Figure 4:
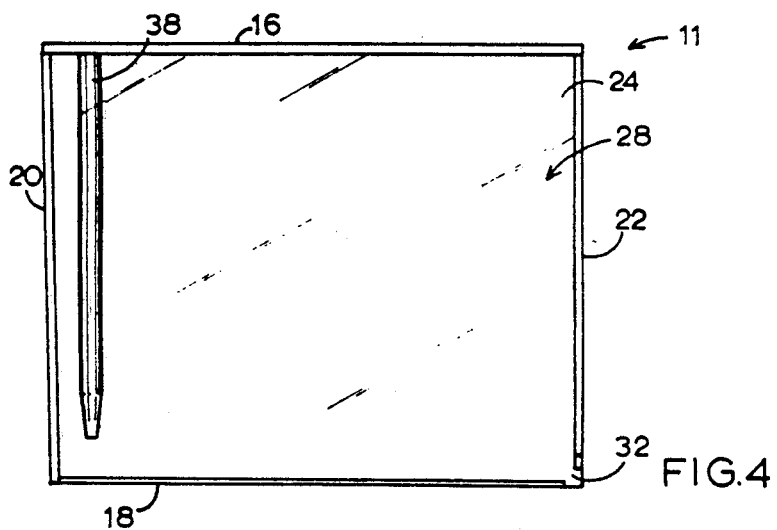
FIG. 4 is similar to FIG. 2 except the module is empty.

Module 11 is shown in more detail in FIGS. 2, 3 and 4. FIG. 2 is a side view of module 11, FIG. 3 is an end view, and FIG. 4 is a side view of module 11 when it is empty. In FIGS. 2, 3 and 4 module 11 is constructed of clear plastic so that its interior may be seen.

Module 11 includes an upper wall 16, a lower wall 18, a rear wall 20, a front wall 22, and side walls 24, 26. These walls define a cavity or chamber 28 in which orthodontic devices, such as device 30, may be stored.

In module 11, the devices are dispensed through a presenting/dispensing aperture 32. Aperture 32, as seen in FIG. 3, contains an upper portion 34 and a lower portion 36. The upper portion has a narrower side-to-side dimension than the lower portion. The upper portion allows a device to be presented but does not allow the entire device to be dispensed. Specifically, the upper portion only allows a tongue 37 of an orthodontic device to extend out of the module. Lower portion 36 is large enough to permit an entire device to be dispensed.

As shown in FIGS. 2 and 3, the devices to be dispensed are stacked on top of each other and touch each other due to gravity. After a device has been dispensed, gravity causes the remaining devices to move down so that the next device may be dispensed.

The devices are directed to the position where they can be dispensed by the side walls and by a guide structure 38. Structure 38, best seen in FIG. 4, is an elongate rod with a tapered end that is connected to upper wall 16. It extends down toward lower wall 18 a predetermined distance, but does not touch it. Structure 38 prevents the orthodontic devices within the module from tipping and moving out of position. Structure 38 and the side walls operate with the orthodontic devices and guide them to a position ready for dispensing. Structure 38 does not touch the bottom two devices so that they may be presented and dispensed.

Dispenser 10 also includes a stand 40. Module 11 is connected to stand 40 by sliding into grooves 42, 44. Grooves 42, 44 act as a vertical track in which module 11 is mounted. Specifically, module 11 has two flanges 46 on its rear wall. The flanges extend perpendicularly away from the module's side walls. Flanges 46 support module 11 in grooves 42, 44.

As can be seen in FIG. 3, flanges 46 are tapered from top to bottom. Accordingly, module 11 is slid into grooves 42, 44 until the taper of the flanges stops the module. In this manner, module 11 is supported on stand 40 and may be slid out when empty and easily replaced with a new module. Modules 12–14 are mounted to stand 40 in the same fashion.

Stand 40 also includes a vertical portion 48 and a horizontal portion 50. Dispenser 10 may be mounted to a wall along portion 48 or to a flat surface along portion 50 by an adhesive.

Figure 5:
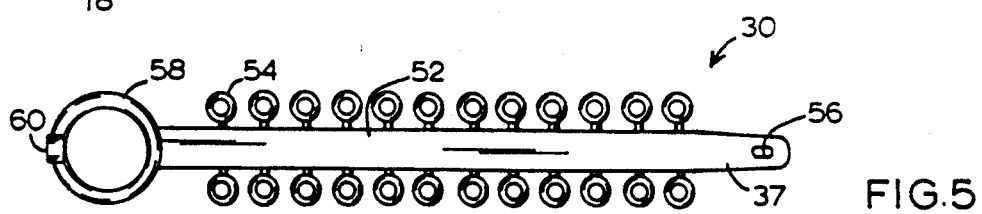
FIG. 5 is a top view of a device which may be dispensed by the invented dispenser.

FIG. 5 shows at 30 a top plan view of an orthodontic device designed to be dispensed by the invented dispenser. Device 30 includes a manipulation carrier or stick 52 along which a plurality of intra-oral units or O-rings, such as O-ring 54, are connected. The O-rings are easily detached from the carrier when used. The tongue 37 of device 30 is also shown.

Device 30 is typically made of an elastomeric material and may be approximately 3 ¼" long. Device 30 includes an aperture 56 through which a tool may be inserted to facilitate handling and dispensing of the device. Device 30 also includes an eyelet 58. Eyelet 58 fits around guide structure 38 in module 11, thereby allowing structure 38 to guide device 30 to its dispense position.

Device 30 also has a tooth 60 which extends above the upper surface of the device. Tooth 60 is used to create friction with another device when it is dispensed from module 11.

Figure 6:
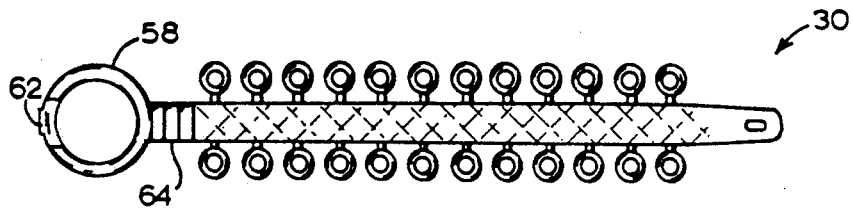
FIG. 6 is a bottom view of the device of FIG. 5.

FIG. 6 is a bottom view of device 30. A channel 62 exist within eyelet 58 to allow a tooth 60 in another device to slide past. Device 30 also includes ridges 64 which are used to contact a tooth 60 on another device and create friction. Accordingly, because the devices are stacked in the module, when one device is dispensed its tooth contacts the ridges of the immediately superior device and pulls the superior device into a presented position. The elastomeric nature of device 30 allows the tooth of one device to move past the ridges of the superior device when the superior device is stopped.

Figure 7:
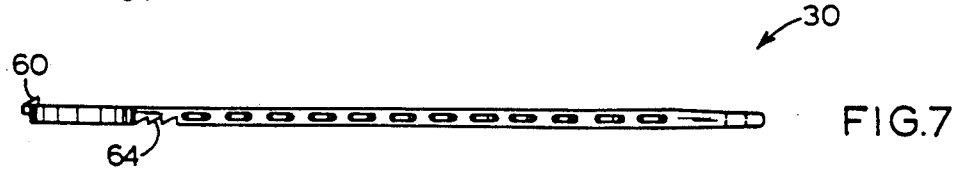
FIG. 7 is a side view of the device of FIG. 5.

FIG. 7 is a side view of device 30 showing ridges 64 and tooth 60.

Operation

The invented anti-contamination orthodontic device dispenser may be mounted to a counter or wall and may be designed to hold one or several modules. Each module contains orthodontic devices to be dispensed. Initially, each module has a bottom seal which must be removed. Withdrawing the seal advances the first device into its dispense position.

When an orthodontist desires a device, he simply grasps the tongue of the device extending from the module and pulls. As the orthodontist pulls, the device contacts the immediately superior device and pulls it a predetermined distance out of the module. The immediately adjacent device is stopped from being pulled completely out of the module by the limited upper dimension of the dispensing aperture. The orthodontist continues pulling until the device is completely withdrawn from the module. Thereafter, the remaining devices move down under gravity and the next device is presented ready for dispensing. In this manner, devices are presented and dispensed in seriatim. The process of presenting and dispensing may be thought of as a dispense cycle.

In this manner, orthodontic devices are dispensed in patient-specific cohesive groups without an orthodontist touching either the dispenser or any devices apart from the one being dispensed. Accordingly, anti-contamination of the remaining devices is assured.

When a module is empty, it is removed from the stand and replaced with another full module.

While the best mode and preferred embodiment of the invention have been described, variations may be made without departing from the spirit of the invention.

It is claimed and desired to secure by Letters Patent:

1. Anti-contamination-seriatim, presenting/dispensing apparatus for plural orthodontic devices capable of allowing dispensing solely through external contact which is limited to contact with a device in the apparatus, where each device includes at least one intra-oral unit and a manipulation carrier detachably joined to and bearing such unit, such carrier including a tongue extending a certain distance from adjacent to beyond such units, said apparatus comprising:
    an anti-contamination container including presenting/dispensing aperture structure, and
    guide structure formed with said container and cooperable with said aperture structure to direct successive devices held within said container, successively in time, to a pair of predispense conditions including a terminal predispense (presented) condition, and a preterminal predispense (non-presented) condition,
    each next-to-be dispensed device being presented in its presented condition via frictional contact occurring between interengageable components formed on adjacent devices within said container.

2. The apparatus of claim 1, wherein said aperture structure has an upper portion large enough to permit only such a tongue to be presented, and a lower portion large enough to permit dispensing of a device.

3. The apparatus of claim 1, wherein such carriers each have an eyelet at one end, and wherein said guide structure comprises a rod, connected to and within said container, passing through each carrier's eyelet, except the next carriers that are to be dispensed.

4. The apparatus of claim 1, further including a stand supporting said container.

5. The apparatus of claim 1, wherein the interengageable components, vis-a-vis a pair of adjacent devices, include a tooth on one device and ridges on the other device.

6. Anti-contamination-seriatim, presenting/dispensing apparatus for plural orthodontic devices capable of allowing dispensing solely through external contact which is limited to contact with a device in the apparatus, where each device includes at least one intra-oral unit and a manipulation carrier detachably joined to and bearing such unit, such carrier including a tongue extending a certain distance from adjacent to beyond such units, said apparatus comprising:
    an anti-contamination container including presenting/dispensing aperture structure, and guide structure formed with said container and cooperable with said aperture structure to direct successive devices held within said container, during use of the apparatus, in such a manner that, at the initiation of a dispense cycle, the tongue of the carrier in one device only, is presented for access on the outside of said aperture structure, and performance of such a cycle effects withdrawal alone of said one only device, with simultaneous shifting of the immediately adjacent device in said container to the same presented-for-access condition just held by its just-dispensed neighbor, each next-to-be dispensed device being presented in its presented condition via frictional contact occurring between interengageable components formed on adjacent devices within said container.

7. The apparatus of claim 6, wherein said aperture structure has an upper portion large enough to permit only such a tongue to be presented, and a lower portion large enough to permit dispensing of a device.

8. The apparatus of claim 6, wherein such carriers each have an eyelet at one end, and wherein said guide structure comprises a rod, connected to and within said container, passing through each carrier's eyelet, except the next carriers that are to be dispensed.

9. The apparatus of claim 6, further including a stand supporting said container.

10. The apparatus of claim 6, wherein the interengageable components, vis-à-vis a pair of adjacent devices, include a tooth on one device and ridges on the other device.

* * * * *

UNITED STATES PATENT AND TRADEMARK OFFICE
CERTIFICATE OF CORRECTION

PATENT NO.   :   5,016,766

DATED        :   May 21, 1991

INVENTOR(S)  :   Douglas J. Klein and Paul E. Klein

It is certified that error appears in the above-identified patent and that said Letters Patent is hereby corrected as shown below:

On the cover page, after "[76] Inventor:" insert --Douglas J. Klein, 901 Lake Shore Rd. and--; after "928 Lake Shore Rd.," insert --both of--; and change "Lak" to --Lake--.

Signed and Sealed this

Twentieth Day of October, 1992

*Attest:*

DOUGLAS B. COMER

*Attesting Officer*   Acting Commissioner of Patents and Trademarks